(12) United States Patent
Lambert et al.

(10) Patent No.: US 9,915,591 B2
(45) Date of Patent: Mar. 13, 2018

(54) METHODS FOR SAMPLING FROM NON-ATMOSPHERIC VESSELS IN A PARALLEL REACTOR SYSTEM

(71) Applicant: Unchained Labs, Pleasanton, CA (US)

(72) Inventors: Stephen Lambert, Castro Valley, CA (US); John F. Varni, Los Gatos, CA (US); Gregor Hsiao, San Jose, CA (US)

(73) Assignee: Unchained Labs, Pleasanton, CA (US)

( * ) Notice: Subject to any disclaimer, the term of this patent is extended or adjusted under 35 U.S.C. 154(b) by 0 days.

(21) Appl. No.: 14/888,021

(22) PCT Filed: Sep. 18, 2013

(86) PCT No.: PCT/US2013/060333
§ 371 (c)(1),
(2) Date: Oct. 29, 2015

(87) PCT Pub. No.: WO2014/178897
PCT Pub. Date: Nov. 6, 2014

(65) Prior Publication Data
US 2016/0076977 A1   Mar. 17, 2016

Related U.S. Application Data

(60) Provisional application No. 61/817,670, filed on Apr. 30, 2013.

(51) Int. Cl.
*G01N 1/18* (2006.01)
*G01N 35/10* (2006.01)
(Continued)

(52) U.S. Cl.
CPC ........... *G01N 1/10* (2013.01); *B01F 13/0836* (2013.01); *B01J 19/0046* (2013.01); *C40B 60/12* (2013.01); *C40B 60/14* (2013.01); *G01N 35/10* (2013.01); *B01J 2219/00283* (2013.01); *B01J 2219/00373* (2013.01); *B01J 2219/00376* (2013.01); *B01J 2219/00389* (2013.01);
(Continued)

(58) Field of Classification Search
CPC . G01N 1/10; G01N 35/10; B01J 2219/00373; B01J 2219/00376; B01J 2219/00389; B01J 2219/00277
See application file for complete search history.

(56) References Cited

U.S. PATENT DOCUMENTS 3,757,981 A   9/1973   Harris, Sr. et al.
5,431,067 A   7/1995   Anderson et al.
(Continued)

FOREIGN PATENT DOCUMENTS

DE   29719919 U1   4/1999
WO   2013148669 A1   10/2013
WO   WO-2014/178897 A1   11/2014

OTHER PUBLICATIONS

International Search Report and Written opinion of the International Search Authority regarding PCT/US2013/060333 dated Jan. 31, 2014; pp. 11.
(Continued)

*Primary Examiner* — Paul S Hyun
(74) *Attorney, Agent, or Firm* — Cooley LLP

(57) ABSTRACT

Methods for sampling reactor contents in parallel reactor systems are disclosed. The methods may be used to sample reactor contents in non-atmospheric (e.g., pressurized) reaction vessels.

20 Claims, 18 Drawing Sheets

(51) Int. Cl.
*C40B 60/14* (2006.01)
*G01N 1/10* (2006.01)
*B01J 19/00* (2006.01)
*C40B 60/12* (2006.01)
*B01F 13/08* (2006.01)
*G01N 13/00* (2006.01)

(52) U.S. Cl.
CPC ............... *B01J 2219/00481* (2013.01); *G01N 2001/105* (2013.01); *G01N 2013/006* (2013.01)

(56) References Cited

U.S. PATENT DOCUMENTS

| | | | |
|---|---|---|---|
| 6,045,755 | A | 4/2000 | Lebl et al. |
| 6,455,315 | B1 | 9/2002 | Baszczynski et al. |
| 6,455,316 | B1 | 9/2002 | Turner et al. |
| 6,524,995 | B2 | 2/2003 | Spaether et al. |
| 6,730,753 | B2 | 5/2004 | Fottinger et al. |
| 6,800,581 | B2 | 10/2004 | Ledford et al. |
| 6,818,584 | B2 | 11/2004 | Garoff et al. |
| 7,381,779 | B2 | 6/2008 | Campbell, Jr. et al. |
| 7,393,806 | B2 | 7/2008 | Bradley et al. |
| 7,465,775 | B2 | 12/2008 | Vestberg et al. |
| 7,666,810 | B2 | 2/2010 | Wang |
| 7,687,426 | B2 | 3/2010 | Bradley et al. |
| 2001/0016631 | A1 | 8/2001 | Freitag et al. |
| 2002/0106813 | A1 | 8/2002 | Smith et al. |
| 2003/0152489 | A1 | 8/2003 | Gueller et al. |
| 2003/0211016 | A1 | 11/2003 | Dales et al. |
| 2007/0066772 | A1 | 3/2007 | Foettinger et al. |
| 2007/0224641 | A1 | 9/2007 | Campbell |
| 2008/0286171 | A1 | 11/2008 | Diamond et al. |
| 2009/0292089 | A1 | 11/2009 | Vaananen et al. |
| 2015/0045210 | A1 | 2/2015 | Giaquinta et al. |

OTHER PUBLICATIONS

International Search Report dated Aug. 6, 2013, for PCT Application No. PCT/US2013/033861, filed on Mar. 26, 2013, 3 pages.
Non-Final Office Action dated Oct. 19, 2016, for U.S. Appl. No. 14/388,401, filed Sep. 26, 2014, 9 pages.
Written Opinion of the International Searching Authority dated Aug. 6, 2013, for PCT Application No. PCT/US2013/033861, filed on Mar. 26, 2013, 6 pages.

METHODS FOR SAMPLING FROM NON-ATMOSPHERIC VESSELS IN A PARALLEL REACTOR SYSTEM

CROSS-REFERENCE TO RELATED APPLICATION

This application is a National Stage application of International Application No. PCT/US2013/060333, filed on Sep. 18, 2013, which claims priority to U.S. Provisional Patent Application No. 61/817,670 filed on Apr. 30, 2013 the disclosure of which is hereby incorporated by reference in its entirety.

FIELD OF THE DISCLOSURE

The field of the disclosure relates to methods for sampling reactor contents in parallel reactor systems and, in particular embodiments, for sampling reactor contents in pressurized reaction vessels.

BACKGROUND

Research and development programs directed at discovery of materials use high-throughput screening tools to evaluate multiple different candidate materials and/or process conditions to reduce the costs and time associated with the identification of promising candidate materials and/or process conditions. Various high-throughput parallel reactor systems have been developed to evaluate multiple candidate materials and/or process conditions by conducting multiple reactions in parallel (i.e., during the same or overlapping time periods).

A continuing need exists for methods for sampling reaction vessel contents in parallel reactor systems that are capable of sampling when the contents of the reaction vessels are pressurized.

SUMMARY

One aspect of the present disclosure is directed to a method for sampling a non-atmospheric reaction vessel of a parallel reactor system. The reactor system includes a reactor array comprising at least two reaction vessels, antechambers disposed above each reaction vessel, antechamber sealing members, a port valve disposed between each antechamber and each reaction vessel and a sampling system for sampling material from the reaction vessels. The sampling system includes a sampling pump, a sampling needle having a tip and a sampling valve disposed between the sampling pump and the tip. The sampling needle is lowered into an antechamber to form a substantially fluid-tight seal between the antechamber sealing member and the sampling needle. The sampling needle is lowered into the reaction vessel having reactor material therein. Material from the reaction vessel is introduced into the sampling needle to form a sampling slug. The sampling needle is raised to position the tip of the sampling needle in the antechamber. The port valve is closed after the tip of the sampling needle is positioned in the antechamber. The slug is retracted so that a first portion is disposed between the sampling valve and the sampling pump and a second portion is disposed between the sampling valve and the tip of the sampling needle. The slug is discharged into a target substrate.

Various refinements exist of the features noted in relation to the above-mentioned aspects of the present disclosure. Further features may also be incorporated in the above-mentioned aspects of the present disclosure as well. These refinements and additional features may exist individually or in any combination. For instance, various features discussed below in relation to any of the illustrated embodiments of the present disclosure may be incorporated into any of the above-described aspects of the present disclosure, alone or in any combination.

BRIEF DESCRIPTION OF THE DRAWINGS

Corresponding reference characters indicate corresponding parts throughout the drawings.

DETAILED DESCRIPTION

Figure 1:
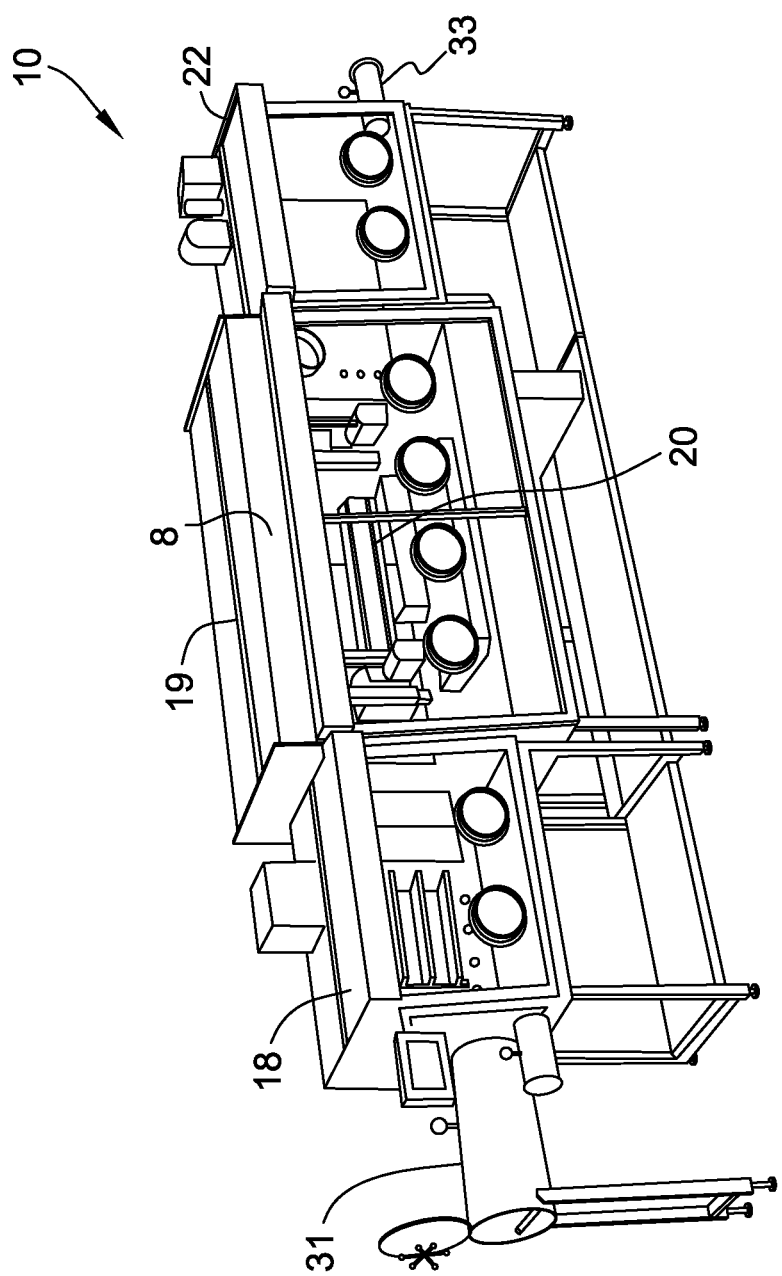
FIG. 1 is a perspective view of a reactor system inside a glove box.

Referring now to FIG. 1, one embodiment of an automated parallel reactor system is generally designated as 10. The parallel reactor system 10 (also referred to herein simply as "reactor system") includes reactor components such as a parallel reactor array 20 within a housing 8 which is commonly referred to in the art as a "glove box." The housing 8 of this embodiment is substantially air-tight relative to the surrounding ambient. In other embodiments, the parallel reactor system does not include a glove box (e.g., a housing which holds reactor components such as a reactor array) and it is contemplated that sampling according to this disclosure may occur outside of a glove box.

In embodiments in which the reactor system includes a glove box, a gas (e.g., inert gas such as nitrogen or argon, or alternatively a reactant gas, including without limitation hydrogen used in hydrogenation reactions) may be introduced into the parallel reactor system. The gas may be continuously introduced into an inlet and continuously withdrawn through an outlet (not shown). The housing 8 may be pressurized to prevent ambient gases from entering the housing. In embodiments in which inert gas is used, the inert gas may be treated to remove potential contaminants (water vapor and/or oxygen) by, for example, treating the gases in a scrubbing device.

The reactor system 10 has three sections—a first section 18, a second section (also referred to herein as "main chamber") 19 and a third section 22. The second section 19 of the housing 8 encloses most reactor system components including the reactor arrays, reagents, robotic arms and the like. The first section 18 and third section 22 provide additional working space for the user and may hold ancillary components. The first section 18 and third section 22 may contain reactor components such as trays and individual containers of reagents, reactor components such as liner vials (i.e., test tubes) and impellers. Such components may be added or removed by use of antechambers 31, 33 which are capable of being isolated from the first section 18 and third section 22. Components may then be added to the antechamber (or removed from the antechamber if components are being removed from the system 10) by purging the antechambers 31, 33 with inert gas (i.e., at least one cycle of vacuum and flushing with inert gas) and the pressure equivocated with the first and third sections 18, 22 of the reactor system. The antechambers 31, 33 may then be opened to the second and third sections 18, 22 for adding material to the reaction system 10. The reactor system 10 may have less than three sections and, in some embodiments, has only one section that contains all reactor system components (i.e., the first section 18 and/or third section 22 are optional).

Introducing inert gases into and out of the housing 8 may allow the amount of water vapor in the system 10 to be reduced to less than about 10 ppm or even to less than about 1 ppm. Use of the inert gas may also allow the amount of oxygen in the system to be reduced to less than about 10 ppm or even less than about 1 ppm. However, the reactor system may include more or less water vapor and oxygen without departing from the scope of the present disclosure. Oxygen and water concentrations in the inert gas may be measured and, as in some embodiments, are measured on a semi-continuous or continuous basis.

Figure 2:
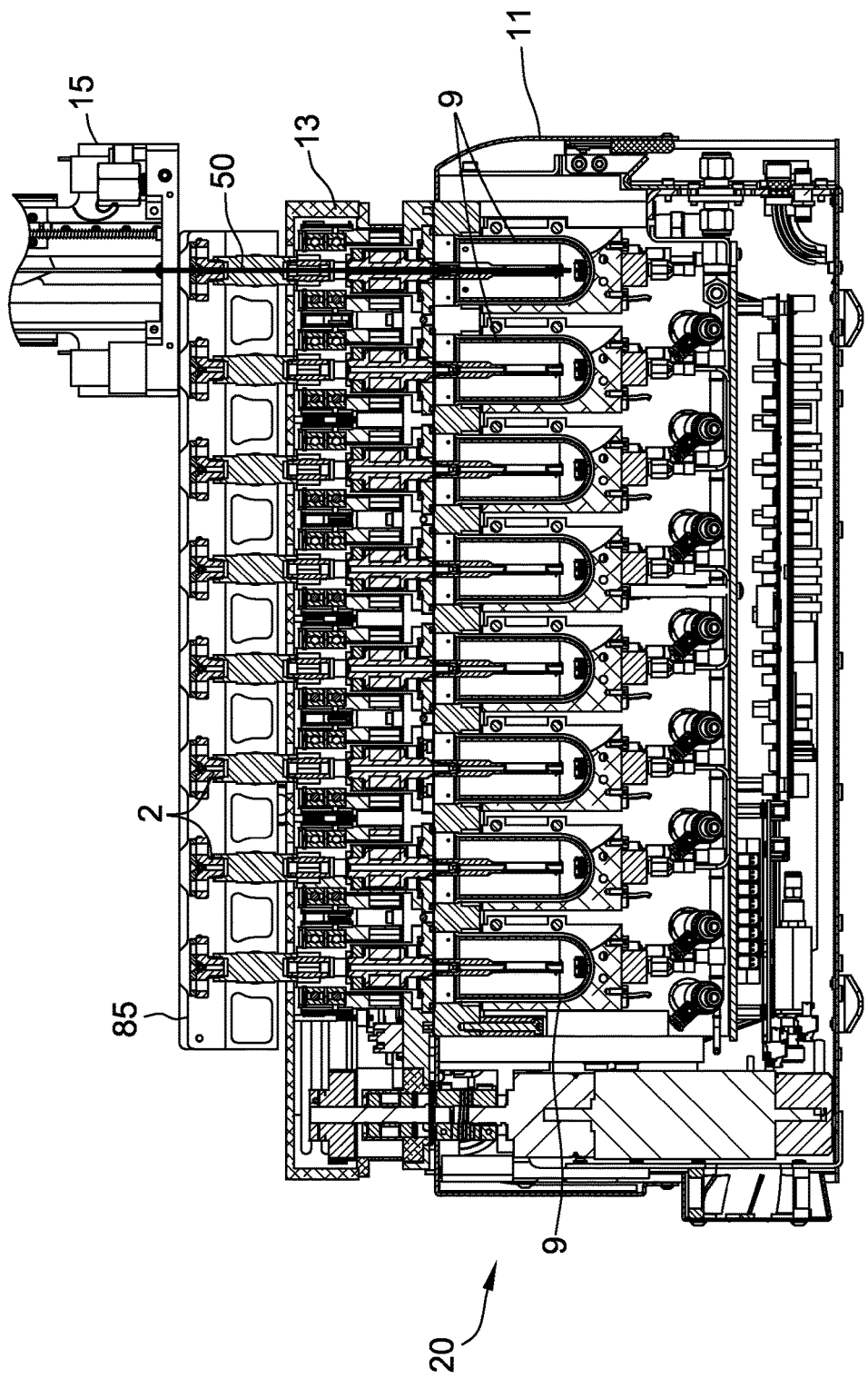
FIG. 2 is a front view of a reactor array and dispensing system.

Referring now to FIG. 2, a reactor array 20 of the reactor system is shown. The reactor array 20 allows for automated control (and, optionally, individual control) of temperature, pressure and stirring such that material (e.g., catalyst) optimization can be performed. The array 20 may be housed in the main chamber 19 of the housing 8. The reactor array 20 includes a number of reaction vessels 9 within a reaction block 11 and a top plate assembly 13 that seals the reaction vessels.

The array 20 shown in FIG. 2 includes eight reaction vessels 9 in a 1×8 arrangement. The array 20 may include two reaction vessels 9 or more, such as in other embodiments, about 4 reaction vessels or more, about 8 reaction vessels or more, about 16 reaction vessels or more or even about 48 reaction vessels or more. The reaction vessels may be in any suitable arrangement (e.g., 1×8, 2×4, 4×4, etc.).

While the reaction vessels 9 are generally shown in the Figures as being reaction vials, it should be understood that other vessels (e.g., wells including wells of microtiter plates and the like) may be used without departing from the scope of the present disclosure.

Figure 9:
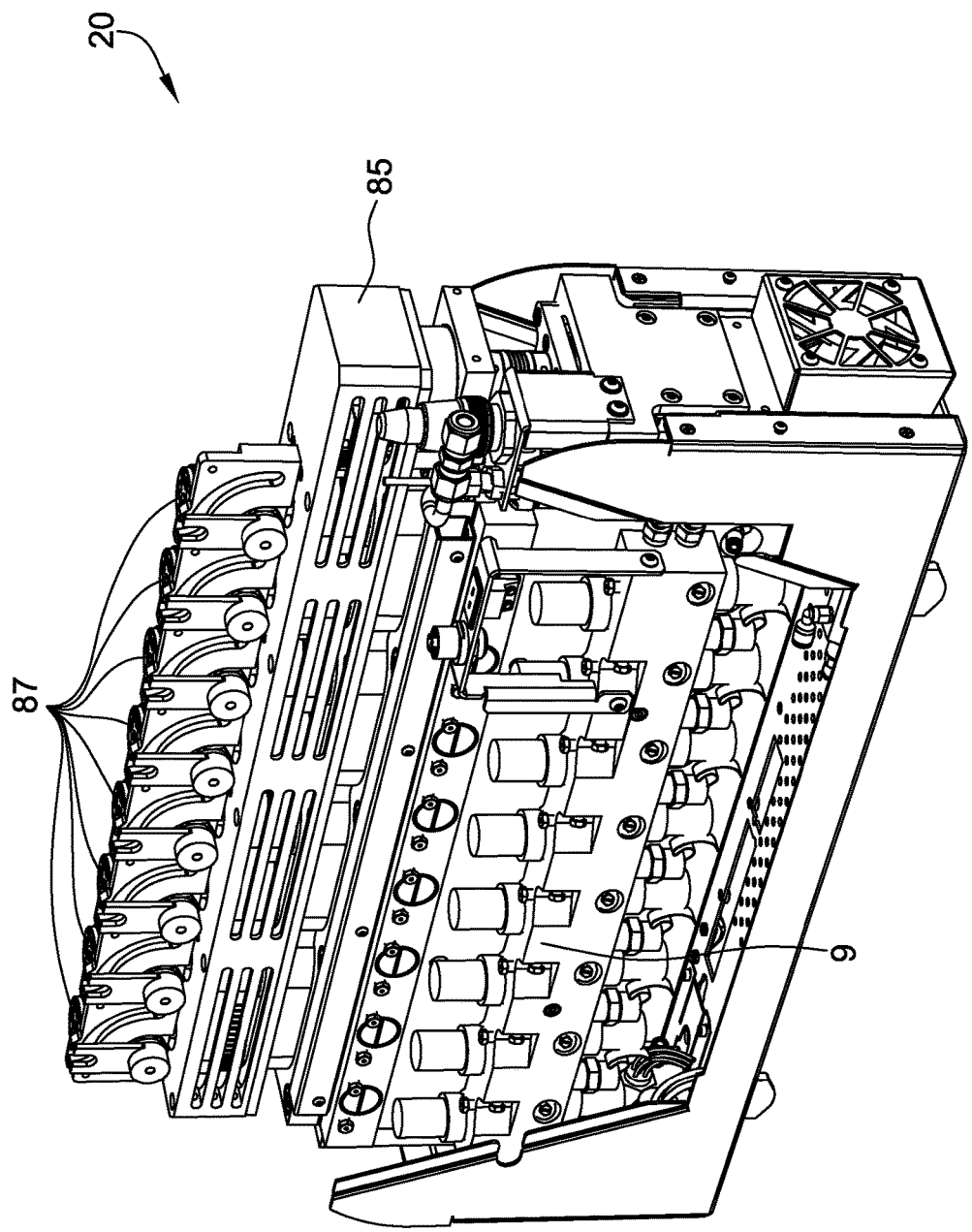
FIG. 9 is a perspective view of a reactor array and injection array.

The reactor array 20 includes an injection array 85 (FIG. 9) that includes access ports 87 and valves that are used to isolate the contents of the reaction vessels 9 during material dispensing and reaction mixture sampling.

Figure 10:
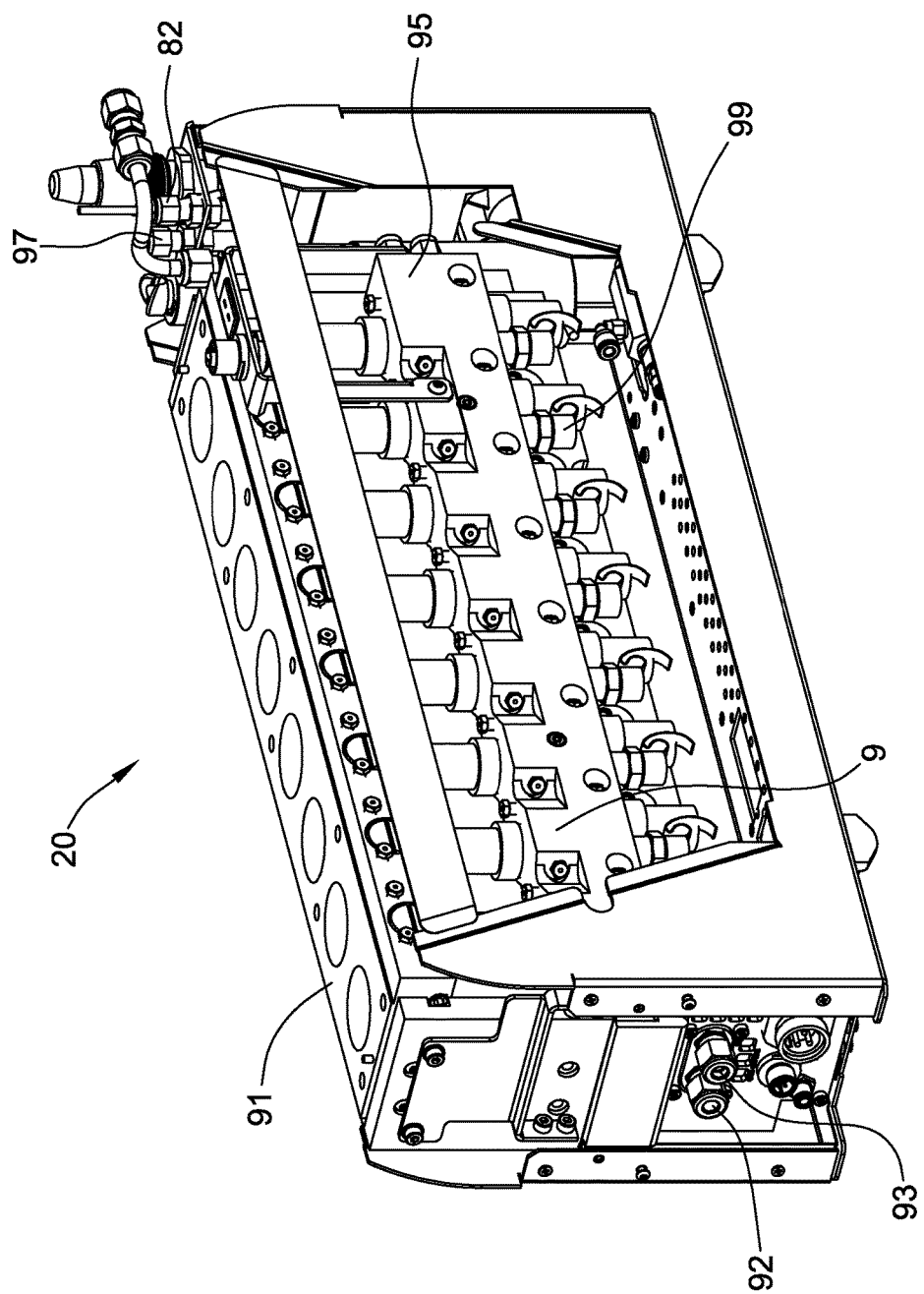
FIG. 10 is a perspective view of the reactor array of FIG. 9.

Referring now to FIG. 10 (the injection array is omitted) the reactor array includes a heated reactor block 91, and a cooling fluid (e.g., gas or liquid) inlet 92 and a cooling fluid outlet 93. In some embodiments, a liquid is used as the cooling fluid for maximum heat transfer. A fluid distribution manifold 79 (FIG. 11) directs cooling fluid around individual reaction vessels 9 so that the temperature within each reaction vessel may be controlled below ambient temperature. In one embodiment the cooling fluid flux (i.e., the temperature gradient between cooling fluid and the reaction vessel contents) to individual reactors may be controlled for maximum thermal response.

The reactor array 20 includes a process gas inlet (i.e., inert gas or reactant gas inlet) 82 and outlet 97 for automatic introduction of a process gas that pressurizes each reaction vessel 9 and provides the ambient for each vessel. Each reaction vessel includes a pressure sensor 99 for measuring and relaying the pressure in each reaction vessel.

Figure 11:
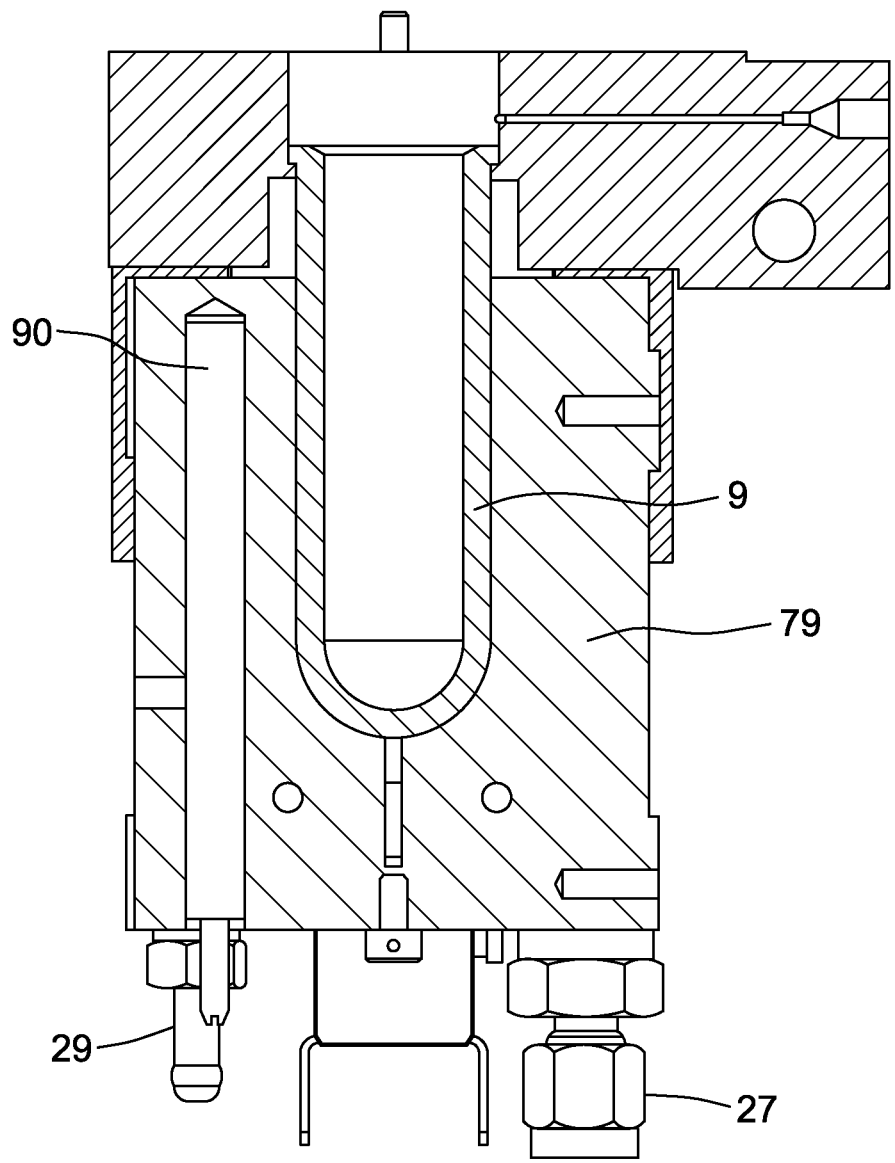
FIG. 11 is a front view of a reaction vessel of the reactor array of FIG. 9.

The array includes cooling channels 30 (FIG. 3) and cooling inlets 27 (FIG. 11) and cooling outlets 29 associated with each reaction vessel 9. The array also includes heated zones 32 (FIG. 3) in thermal communication with each reaction vessel 9 for controlling the temperature of the reaction mixture in the vessel. The heated zones 32 may be heated by use of a cartridge heater 90 (FIG. 11). An external thermocouple (not shown but its position indicated by "79") may be used to indirectly measure the temperature of the reaction contents. The array may include insulation to help regulate the temperature of the reaction mixture.

An automated dispensing system 15 (FIG. 2) is used to dispense material into each reaction vessel 9. The dispensing system 15 is controlled by an arm (not shown) that positions the dispensing system above each reaction vessel 9 for dispensing of material.

Figure 3:
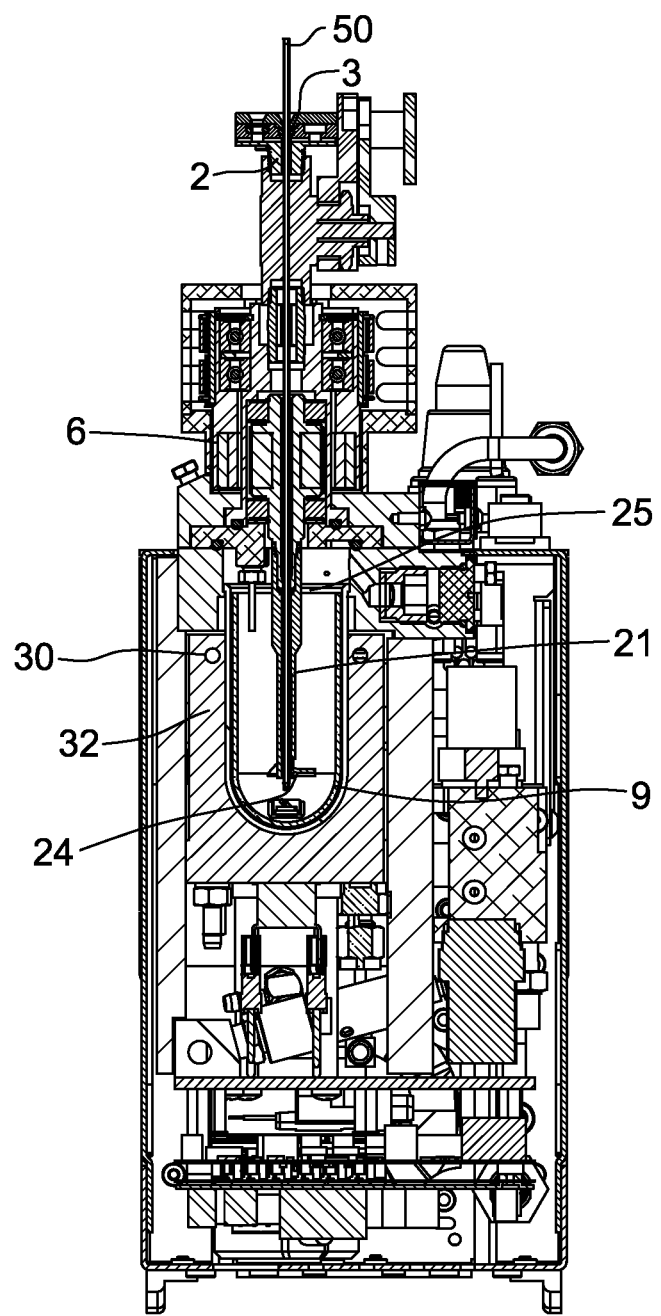
FIGS. 3-4 are front views of a reaction vessel of the array of FIG. 2.

Referring now to FIG. 3, the contents of the reaction vessels 9 may be stirred by use of a magnetic drive 6 which rotates a magnetically coupled stirrer 21. The stirrer 21 may include an impeller 24 to promote stirring of the contents of the reaction vessel 9. The rotation of the magnet 6 causes a corresponding magnet in the reaction vessel to rotate along with a stirrer 21 attached to the magnet thereby stirring the contents of the reaction vessel 9. In some embodiments and as shown in FIG. 3, the stirrer 21 extends from an upper end 25 of the reaction vessel 9 and does not contact the walls of the reaction vessel during use.

Figure 4:
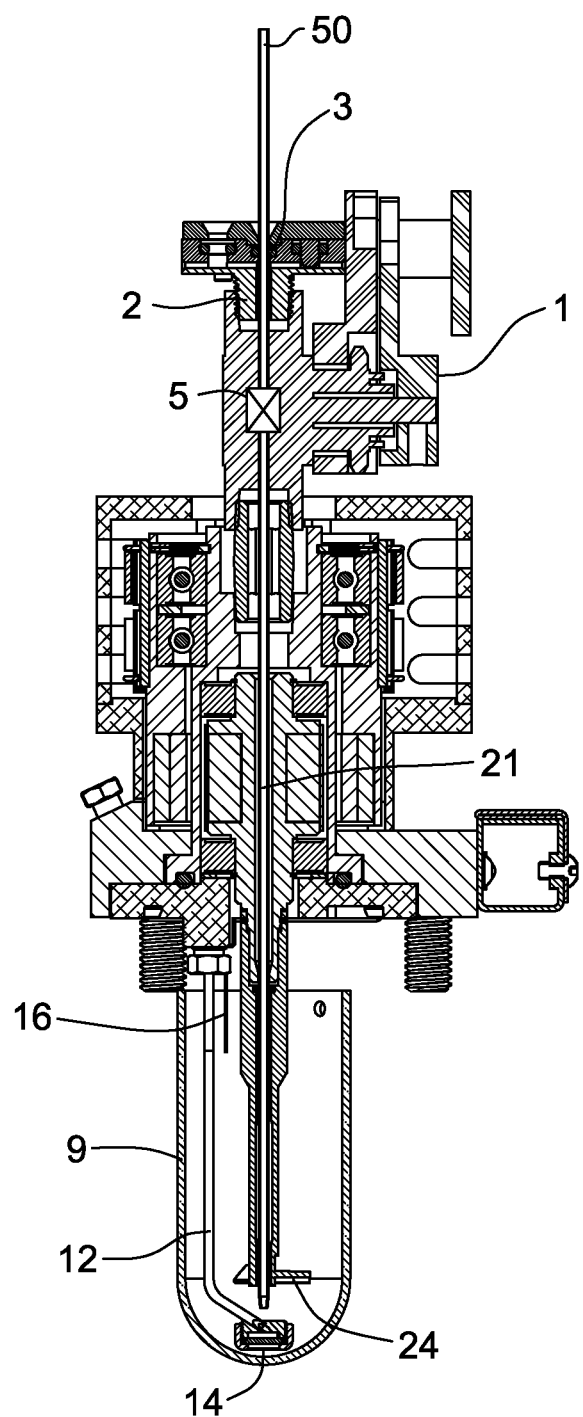
Figure 5:
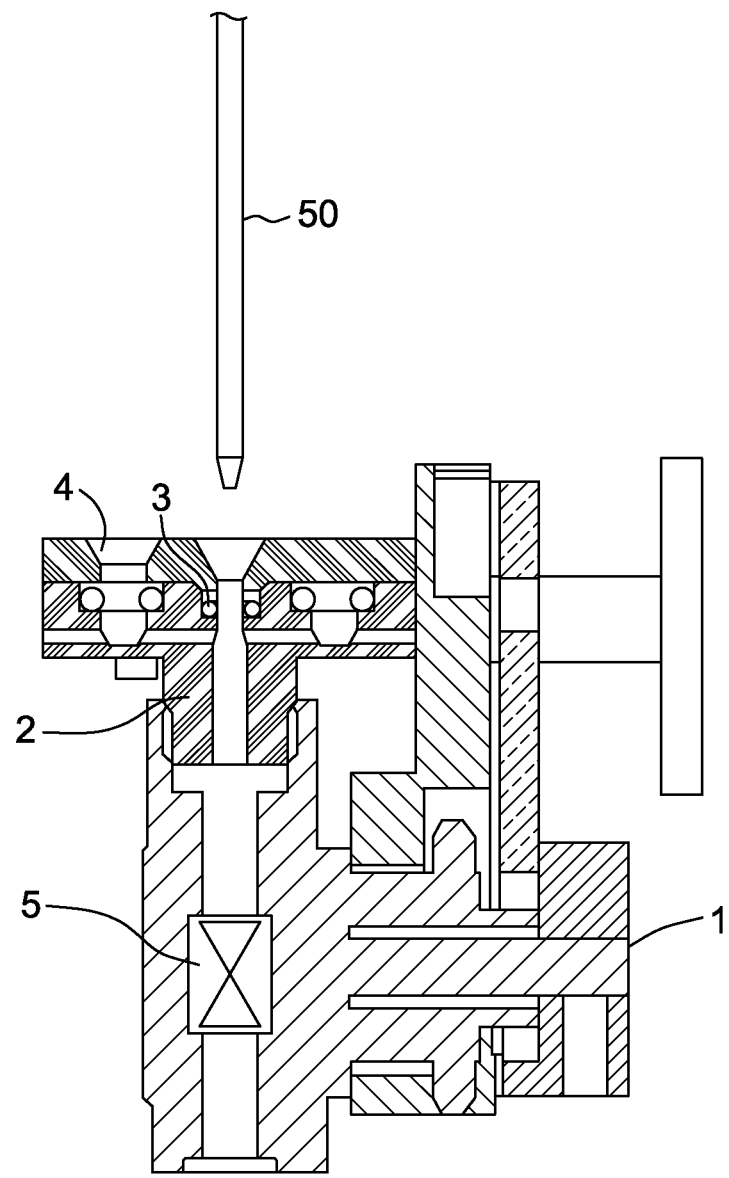
FIG. 5 is a front view of the top plate assembly of the array showing a sealing member, antechamber, and port valve prior to insertion of an injection needle.

The reactor array may include a dip tube 12 (FIG. 4) with a frit 14 in each reaction vessel 9 to remove fluids from the reaction vessel 9. The frit 14 acts to filter solids while withdrawing fluid from the vessel 9. The frit 14 may periodically be backwashed to prevent excess solid material from obstructing the frit 14.

A second tube 16 may be used for injection of solvent. In some embodiments, the tube 16 is eliminated and solvent is introduced through the dip tube thereby backwashing the frit 14.

In some embodiments and as shown in FIGS. 3-7, the parallel reactor system includes a sealing member 3 disposed above each reaction vessel 9. The sealing member 3 forms a substantially fluid-tight seal between an injection needle 50 of the dispensing system 15 (FIG. 2).

Figure 8:
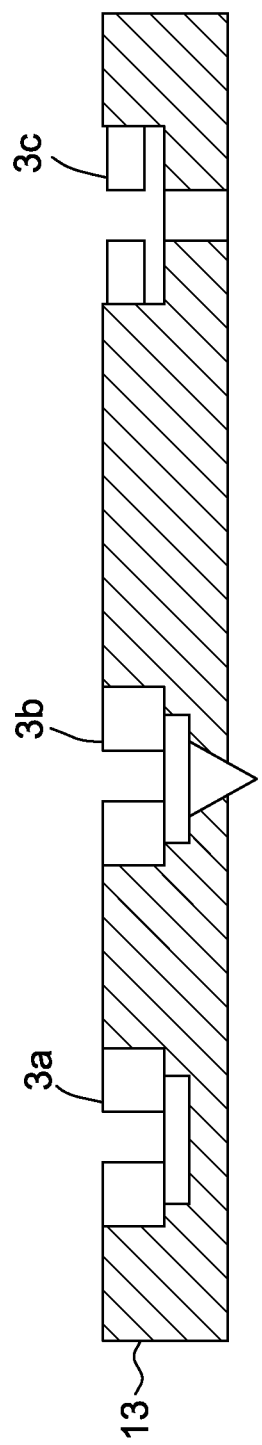
FIG. 8 is a front view of three alternative sealing members for sealing an antechamber.

Suitable alternative sealing members 3 for covering an opening within the top plate assembly 13 above the reaction vessel 9 are shown in FIG. 8. A first embodiment of the sealing member 3 is referenced as 3a in FIG. 8. Sealing member 3a is a septum. To dispense material into the reaction vessel 9, the injection needle 50 (FIG. 2) is lowered and pierces the septum 3a. The septum 3a forms a seal around the injection needle and isolates the reaction vessel from the other components of the parallel reactor system. The injection needle continues to be lowered to dispense material as further described below.

A second embodiment of the sealing member 3 is referenced as 3b in FIG. 8. The top plate assembly 13 may include duckbill injectors 3b that are seated in the openings within the top plate assembly. To dispense material into the reaction vessel 9, the injection needle is lowered and pierces the duckbill injector 3b. The duckbill injector 3b forms a seal around the injection needle and isolates the reaction vessel from the other components of the parallel reactor system. The injection needle continues to be lowered to dispense material as further described below. Once the fluid pressure is reduced, the injector seals which prevents backflow of fluid.

A third embodiment of the sealing member is referenced as 3c in FIG. 8. The top plate assembly 13 may include an o-ring 3c seated in the openings within the top plate assembly. To dispense material into the reaction vessel 9, the injection needle is lowered through the o-ring 3c thereby forming an air-tight seal with the o-ring. The injection needle continues to be lowered to dispense material as further described below. In another embodiment, the sealing member 3 may be a valve (not shown).

Figure 6:
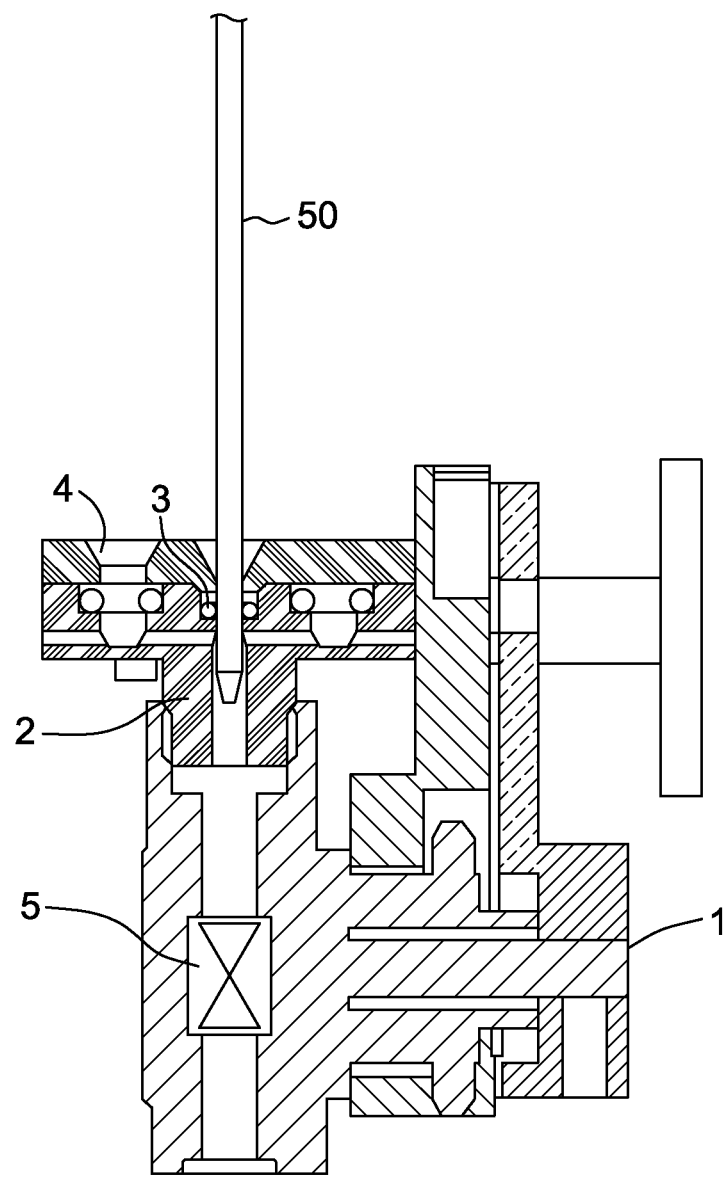
FIG. 6 is a front view of the top plate assembly of the array showing a sealing member, antechamber, and port valve upon insertion of the injection needle into the antechamber.
Figure 7:
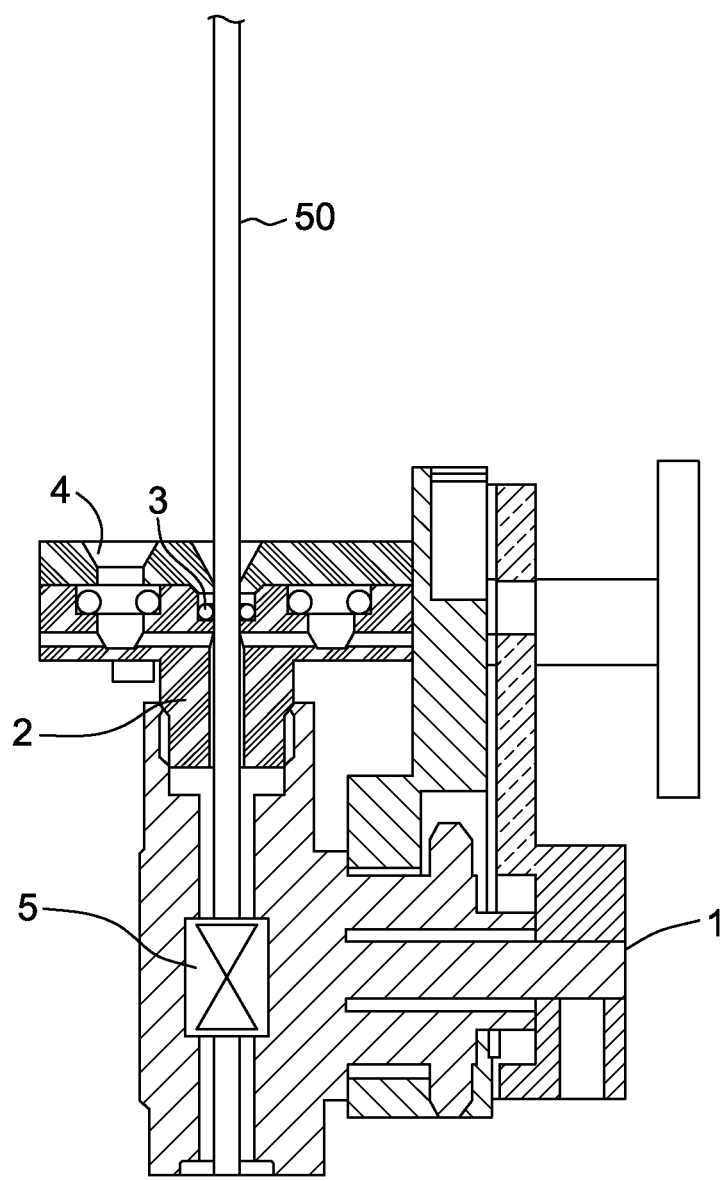
FIG. 7 is a front view of the top plate assembly of the array showing a sealing member, antechamber, and port valve after insertion of the injection needle through the open port valve.

In addition to the sealing member 3, the top plate assembly 13 may include antechambers 2 (FIGS. 2-7) disposed above each reaction vessel 9. The antechambers 2 include inert gas inlets and venting outlets (not shown) for purging the antechamber. Corrosive gases may enter the antechamber 2 during lowering of the needle 50 into the reaction vessel 9 (FIGS. 6-7). The antechamber 2 allows such gases to be isolated and removed (and treated downstream) thereby preventing such gases from contacting other portions of the parallel reactor system.

In addition to the antechamber 2, the top plate assembly 13 may include a port valve 5 (FIGS. 5-7) that isolate the antechamber 2 from the reaction vessel 9 when closed. The port valve 5 may be controlled by an actuating mechanism 1. The port valve 5 may be closed while the injection needle 50 is lowered to engage the sealing member 3 and to enter the antechamber 2. Inert gas may be introduced into the antechamber 2 and withdrawn (optionally while creating a vacuum) to purge the antechamber of any fluid that is present in the needle. A gas manifold pressure system (not shown) attached to the arm of the dispensing system may seal with a port 4 for applying a vacuum and/or applying an inert gas to the antechamber 2.

After the antechamber 2 is purged, the port valve 5 is opened and the needle 50 is lowered toward the reaction chamber 9 (FIG. 7) to dispense material into the reaction chamber. In embodiments in which the reaction vessel 9 is at a pressure other than ambient, the antechamber 2 is pressurized (or a vacuum is applied) to substantially match the pressure of the reaction chamber 9.

After dispensing of material through the injection needle 50 into the reaction vessel, the injection needle is raised until the tip of the injection passes through the port valve 5 into the antechamber 2. Port valve 5 is then closed and the remaining liquid in the needle is quickly drawn back to behind the first valve 71 of the dispensing system 15 (FIG. 12), e.g., by a pump. The antechamber 2 is then purged with inert gas and brought to ambient pressure to purge any vapor that may be present in the needle 50. The injection needle 50 may then be further raised and removed from the top plate assembly 13.

Figure 12:
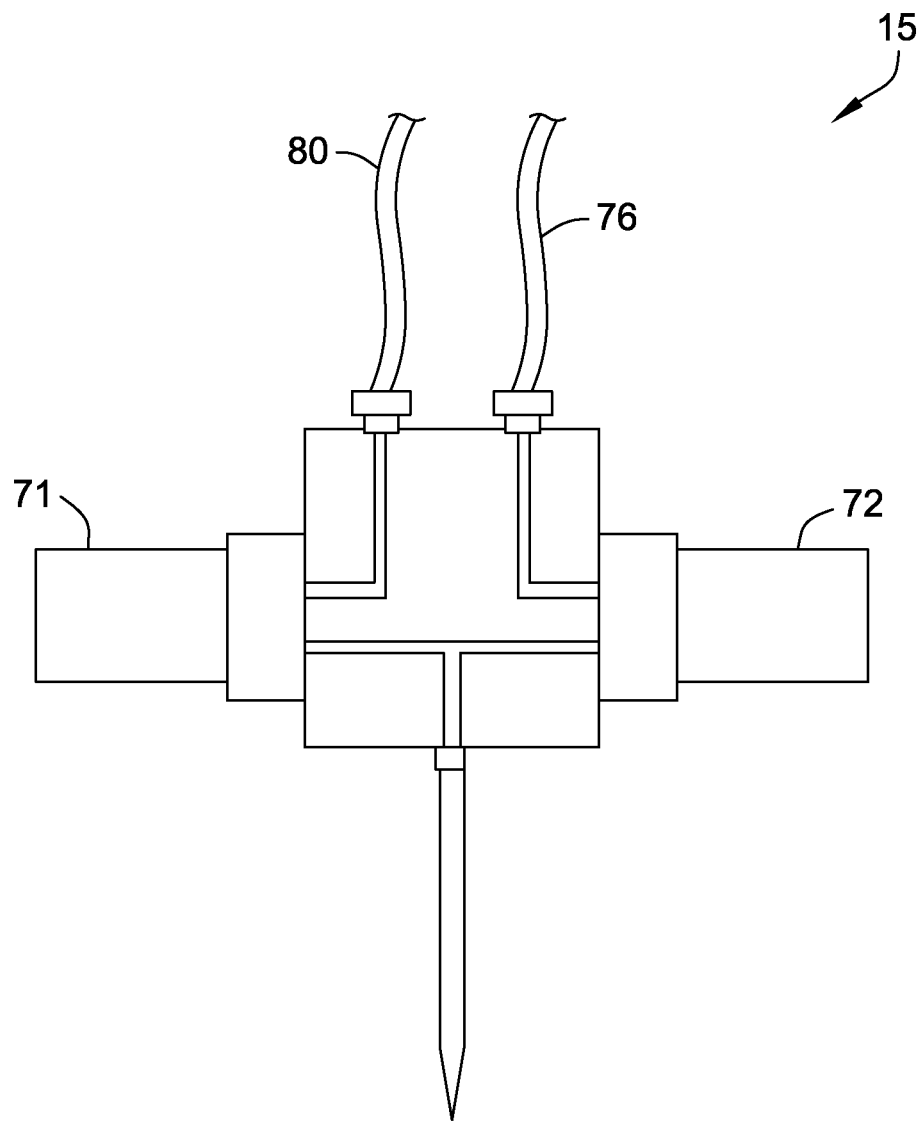
FIG. 12 is a front view of a dispensing system for injecting fluid into the reaction vessels.

Referring now to FIG. 12, an embodiment of a dispensing system 15 for use in dispensing two materials into each reaction vessel is shown. The system 15 includes a first valve 71 used to control flow of a first fluid (e.g., reaction fluid) through a first supply line 80 and a second valve 72 used to control flow of a second fluid (e.g., solvent) through a second supply line 76. The first fluid is generally different than the second fluid. The valves may be electronically or pneumatically actuated. Allowing two fluids to be dispensed by use of one dispensing system reduces cross-contamination (and resulting corrosion) by isolating the corrosive fluid from the surrounding atmosphere and providing a mechanism for the dispensing system to be rinsed by an inert material.

Other embodiments of the dispensing system utilize additional selection style valve(s) beyond those shown in FIG. 12. This allows controlled volumes of different fluids to be contained within a single line and separated by air gaps. In this manner the exact required amount of corrosive fluid can be contained behind the fluid valve described in FIG. 12, followed by an air gap and a non-corrosive solvent type fluid. Upon dispensing, the fluid valve is actuated and enough volume is dispensed to completely expel the corrosive fluid and a small portion of the air gap. After fluid is completely dispensed there is no bulk quantity of the corrosive fluid remaining exposed to the surrounding atmosphere.

Figure 13:
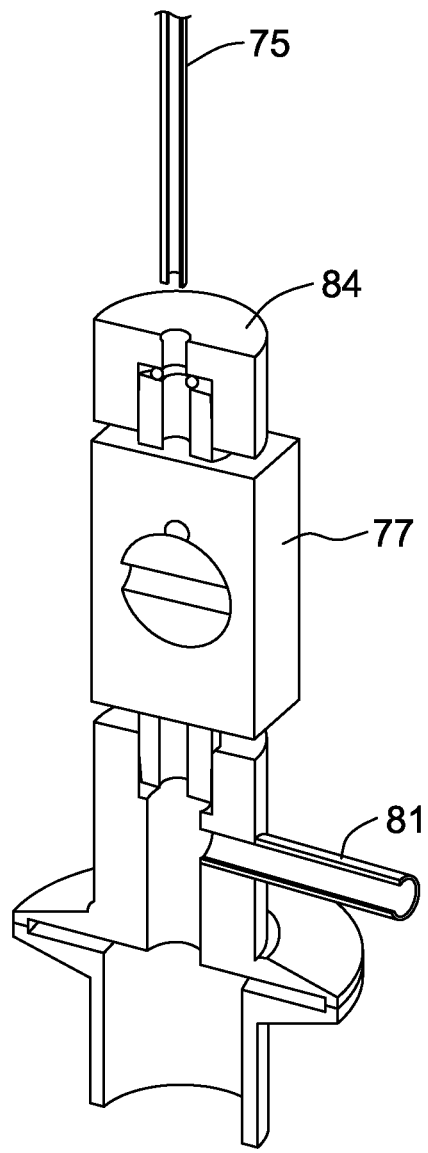
FIG. 13 is a cross-section perspective view of a waste container sealing member prior to insertion of an injection needle.
Figure 14:
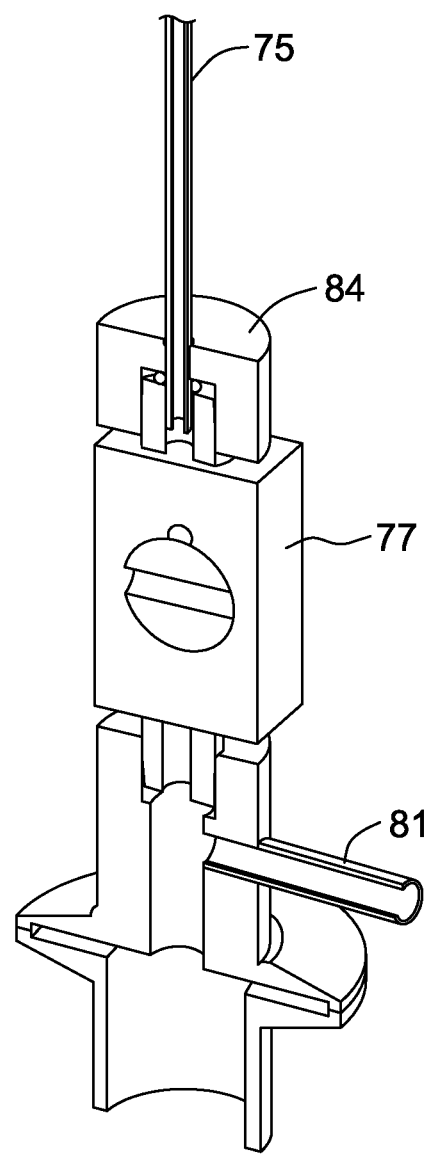
FIG. 14 is a cross-section perspective view of a waste container sealing member after formation of a seal between the injection needle and an o-ring and prior to the port valve opening.
Figure 15:
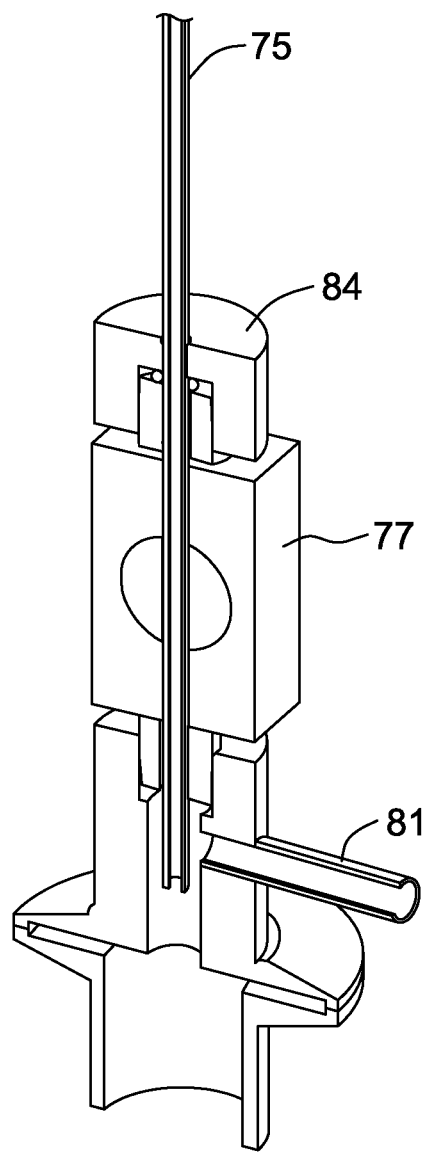
FIG. 15 is a cross-section perspective view of a waste container sealing member after the port valve is opened and the injection needle is fully positioned for dispensing waste.

The parallel reactor system 10 (FIG. 1) may include waste containers for disposal of unreacted reagents or reaction by-products and other corrosive materials. In some embodiments and as shown in FIGS. 13-15, each waste container may be connected to a sealing assembly to prevent material from back filling from the waste container. The waste container sealing assembly includes a sealing member 84 and a valve 77. The sealing member 84 may, for example, be an o-ring which conforms to the size and shape of the dispensing needle 75 or the sealing member may be a septum or duck-bill injector as described above in relation to the sealing member 3 (FIG. 8) of the reactor array 20 (FIG. 2). The reactor system may include two or more such waste containers to prevent the mixing of two different waste streams which are capable of reacting strongly when combined. Switching of flow between waste containers may be achieved by means of selector valve (not shown) which may be actuated by software control, consistent with chemistry steps to avoid mixing of incompatible waste streams.

To inject waste into the waste vessel, the waste dispensing needle 75 is placed through the sealing member 84 to form a primary seal. The valve 77 is opened and the needle 75 is lowered past the valve 77. Fluid is injected into the waste vessel and the dispensing needle 75 is removed from the sealing member 84. The valve 77 is closed before the dispensing needle is removed from the sealing member to prevent back-fill of material from the waste-containers.

The sealing system may include a port 81 for introducing inert gas to the waste vessel. An inert purge gas may be continuously fed to the waste vessel to exclude the surrounding atmosphere and prevent unwanted reaction with that atmosphere. The gas may be treated (e.g., in a neutralization bubbler) and vented (not shown). Neutralization bubblers allow visual verification that venting is occurring. The bubbler may include any liquid (e.g., oil) that may neutralize corrosive gases and/or hazardous gases. After treatment, gases may be vented through a hood. In some embodiments, the atmosphere is venting continuously.

In some embodiments, the waste containers are positioned outside of the main chamber 19 (FIG. 1). The lines between the waste containers and the main chamber 19 are a potential ingress path for surrounding atmosphere. One or more check valves and/or solenoid valves may be used to prevent surrounding atmosphere from entering the main chamber 19. Wastes may be removed from the reaction vessels by pressurizing the reaction vessel above the pressure of the waste container (e.g., by use of an inert gas) to cause waste to flow to the waste container and entirely empty into the waste container.

Figure 16:
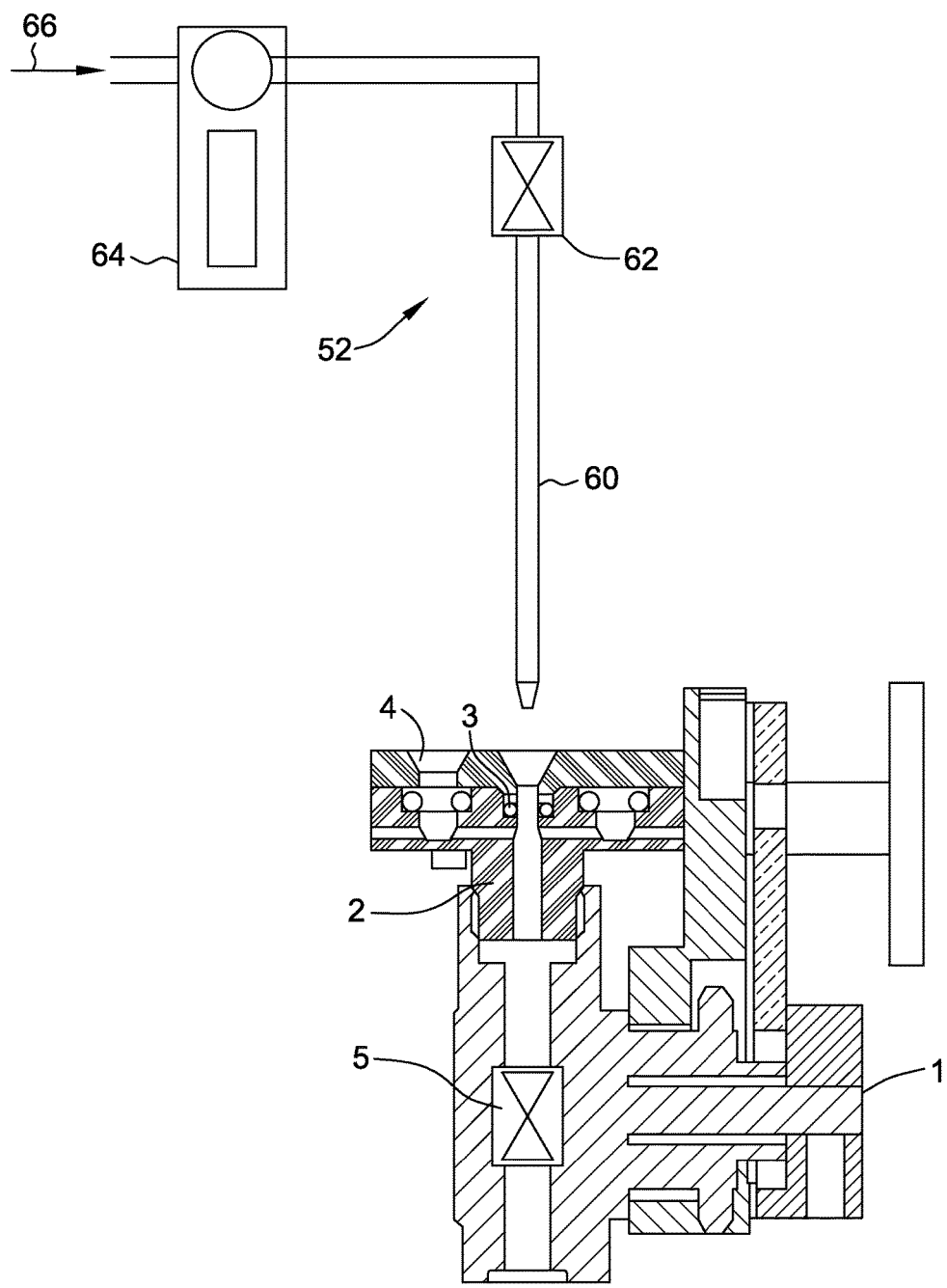
FIG. 16 is a front view of a top plate assembly for sampling reaction vessels and a sampling assembly prior to insertion of a sampling needle.
Figure 17:
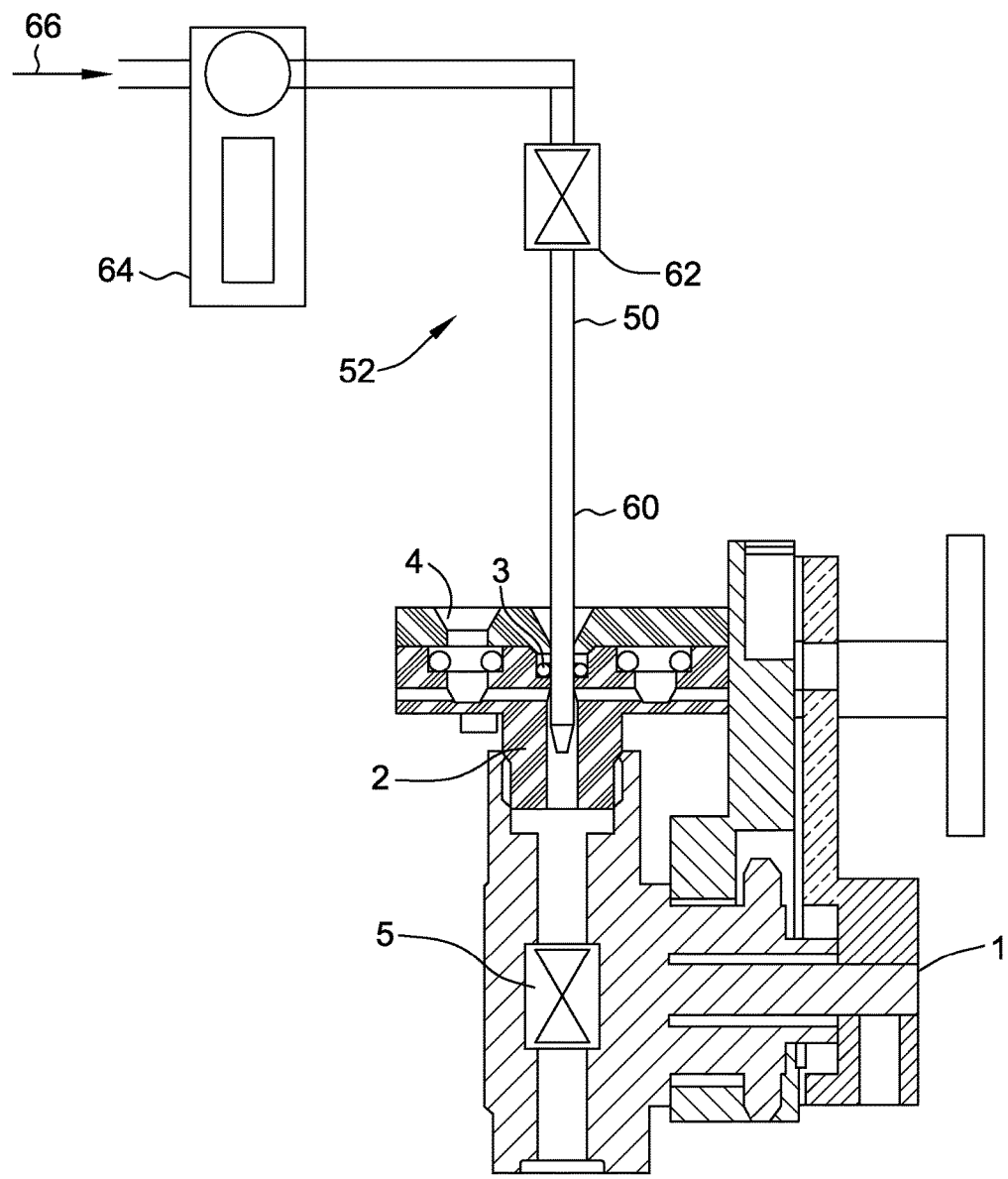
FIG. 17 is a front view of a top plate assembly for sampling reaction vessels and a sampling assembly upon insertion of the sampling needle into the antechamber.
Figure 18:
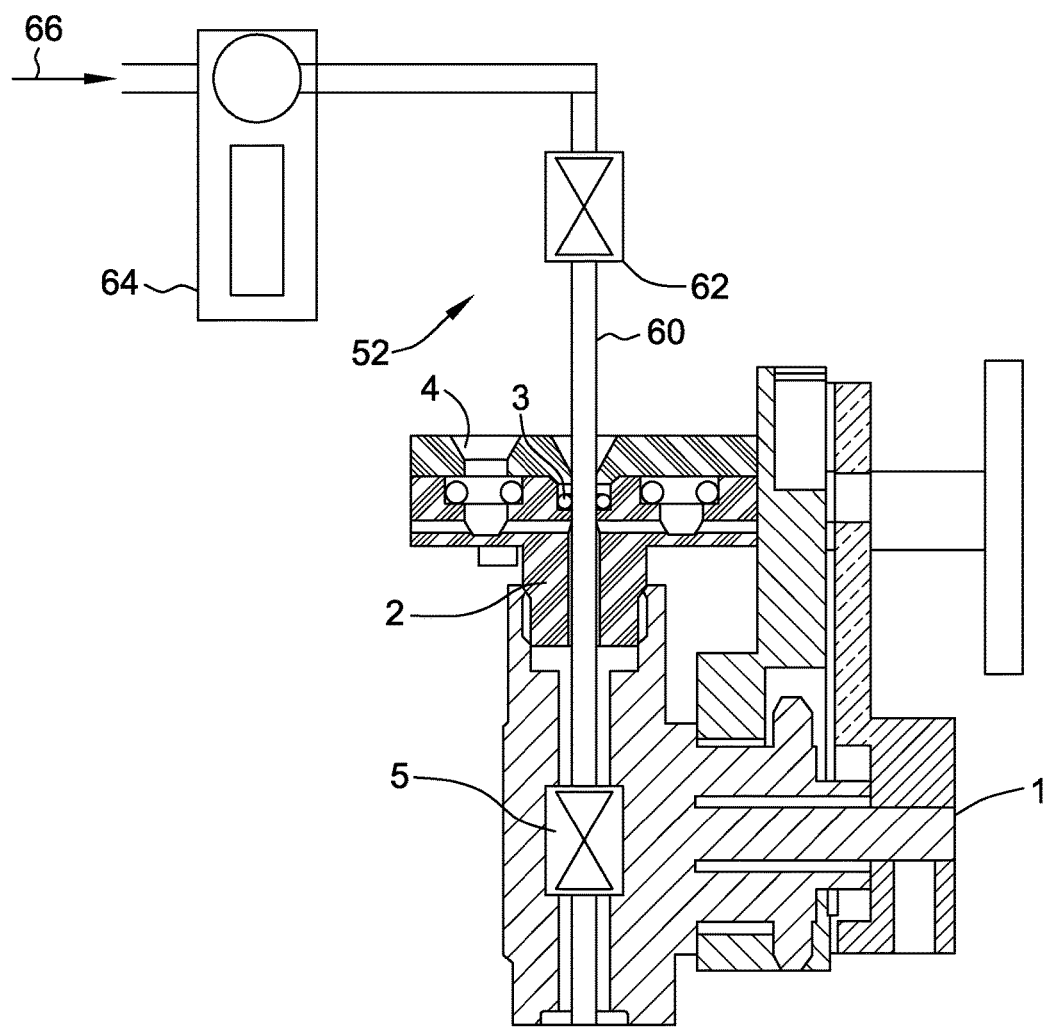
FIG. 18 is a front view of a top plate assembly for sampling reaction vessels and a sampling assembly after insertion of the sampling needle through the open port valve.

The top plate assembly 13 (FIG. 2) may also be used for sampling the contents of the reaction vessels 9 for analysis of the contents. As shown in FIGS. 16-18, the reaction contents are sampled by use of a sampling system 52 that includes a sampling needle 60 having a tip, a sampling pump 64 and a sampling valve 62 disposed between the tip of the needle 60 and the pump 64. The sampling system 60 is typically automated. The pump 64 is in fluid communication with a backing solvent 66 (e.g., any suitable aqueous or organic solvent, typically with relatively low viscosity (e.g., less than about 10 cP)) that is used to aspirate the sample. The pump 64 may be any suitable pump such as a syringe pump that is operable by a drive system (not shown).

To sample the material within the reaction vessel 9 (FIG. 2), the sampling needle 60 is lowered into the antechamber 2 as shown in FIG. 17 to form a substantially fluid-tight seal with the antechamber sealing member 3. With the port valve 5 being closed, fluid is purged from the antechamber 2 by circulating inert gas through the antechamber. The pressure between the antechamber 2 and the reaction vessel 9 (FIG. 2) is equalized (typically by pressurizing the antechamber). In this regard, the present disclosure is not limited to a particular pressure. Pressures up to about 3,500 kPa (about 507 psi) or more may be used without limitation. Alternatively, the reaction vessel 9 may be under vacuum. The reaction vessel may be referred to herein as being "non-atmospheric" which is intended to include embodiments in which the reaction vessel is pressurized or embodiments in which the reaction vessel is under vacuum.

The atmosphere of the reaction vessel 9 may include an inert gas. By purging fluid from the antechamber 2 by circulating inert gas through the antechamber, an inert gas atmosphere may be maintained in the reaction vessel 9 during and after sampling (i.e., the reaction vessel includes an inert atmosphere prior to lowering the sampling needle into the antechamber and the inert atmosphere is maintained at least until the port valve is closed as described below).

Typically the sampling needle 60 is filled with backing solvent (to the top of the needle) when the tip is lowered into the antechamber 2. In embodiments in which the antechamber 2 is pressurized, pressurizing the antechamber 2 causes an amount of vapor to enter the sampling needle 60. This vapor separates the backing solvent from the sampled material during aspiration.

After adjusting the pressure of the antechamber 2 such that the pressure of the antechamber 2 is substantially the same as that of the reaction vessel 9, the port valve 5 is opened and the sampling needle 60 is lowered into the reaction vessel as shown in FIG. 18. The sampling pump 64 is operated to reduce the pressure at the pump. The differential pressure causes an amount of material (which may be referred to herein as a sampling "slug" of material) in the reaction vessel to enter the sampling needle 60. This volume of material may be referred to herein as the "sampling volume."

The sampling needle 60 containing the sample slug is then raised such that the tip of the sampling needle 60 is positioned in the antechamber 2. The port valve 5 is closed after the tip is positioned in the antechamber 2. The pump 64 is operated such that the slug is further retracted into the sampling needle and/or sample lines. The sample is retracted until a first portion (e.g., upstream portion) of the slug is disposed between the sampling valve 62 and the sampling pump 64 and a second portion (e.g., downstream portion) is disposed between the sampling valve 62 and the tip of the sampling needle 60. The amount of back solvent retracted by the pump 64 in order to retract the slug to the targeted position may be referred to herein as the "retraction volume". By not retracting the entire volume of sample past the sampling valve 62, gas is not retracted past the sampling valve. Such gas may interfere with accuracy and precision of dispensed sample volumes (e.g., may prevent the sample slug from moving during the depressurization step described below). Such gas may displace the slug randomly in the line which prevents the slug from dispensed in its entirely without dispensing some of the back solvent. Dispensing the back solvent distorts sample composition and concentration relative to the contents of the reaction vessel.

In some embodiments of the present disclosure, the downstream portion of the slug disposed between the sampling valve 62 and tip of the sampling needle 60 is a sufficiently small size that the downstream portion of the slug is held in the needle 60 by surface tension.

After the slug is further retracted, the pressure in the antechamber 2 is adjusted to equalize the pressure in the housing 8 (FIG. 1) in which the reactor array 20 is mounted. Typically, the reaction vessel 9 is pressurized relative to the housing such that the antechamber 2 is depressurized prior to withdrawal of the sampling needle 60 from the antechamber 2. By adjusting the pressure after the slug is further retracted, dispensing of a portion of the slug into the reaction chamber may be prevented. Vapor may be purged from the antechamber 2 after the port valve is closed by circulating inert gas through the antechamber 2.

After the pressure in the antechamber 2 is adjusted, the sampling needle 60 may be withdrawn from the antechamber 2 (i.e., raising the sampling needle such that the sampling needle disengages the antechamber sealing member 3). The sampling needle 60 may be repositioned to a target substrate (placed above or within such substrate) such as an analysis vessel such as HPLC vials, microtiter plates and the like or an analytical device such as HPLC, gas chromatography unit. In some embodiments, the target substrate is another reaction vessel such as in instances when the first reaction vessel is a reagent or catalyst which is used in the second vessel for further reaction. In this regard, the term "sampling" as used herein includes any method in which material is withdrawn from a reaction vessel for further use including further processing or analysis, unless stated otherwise. The term "sampling" should not be considered in a limiting sense.

Once the sampling needle is repositioned, the pump 64 is operated to depressurize the material upstream of the tip valve 62. This depressurization causes the gas disposed between the sample slug and the backing solvent to expand. This increase in volume may be referred to herein as the "depressurization volume." The sampling valve 62 is opened and the pump 64 is operated to dispense the sampling slug. In addition to the sample volume itself, the retraction volume is dispensed to move at least the volume of the sample. A portion of the depressurization volume may also be dispensed to ensure that the entire sample is dispensed without dispensing back solvent.

The retraction volume and depressurization volumes described above may be determined by empirical methods. The precise volume will depend on the dynamics of the system including the sizing of the injection needle and associated connecting lines, the back solvent, the sampled material and the reaction vessel pressure. The retraction volume may generally increase with increasing reactor pressure due to mechanical compliance in the sampling lines. The depressurization volume (i.e., the volume needed to hold the sample in the sampling system without the sample being further retracted or moving toward the tip upon opening the sampling valve) may be determined by aspirating a volume of sample (optionally with coloring added to indicate the sample in transparent lines), depressurizing a known volume, and determining whether the sample moves downstream or upstream after the sampling valve 62 is opened. The depressurization volume may be adjusted until the sample does not move upstream or downstream upon opening the sampling valve 62.

The parallel reactor system 10 (FIG. 1) may include a number of arms for injecting reagent and/or sampling reaction vessel, e.g., automatically injecting reagent or taking samples, and may include additional reaction vessels, reagent storage and the like. The parallel reactor system may include various supporting elements for securing the components of the system and these supporting elements may be distinct from one another (similar to the housing sections) or may be integrally connected in the system. The system may employ various heating and/or cooling elements for heating and/or cooling the reagents and/or reaction mixtures. Generally these components may be designed and selected in accordance with the principles and standards within the high-throughput parallel processing field. The various components may be linked to a controller (e.g., a microcontroller or computer including computer software) that is configured for automatically operating the parallel reactors, as will be understood by those of skill in the art.

The methods of the present disclosure for sampling reaction vessels of parallel reactor systems have several advantages compared to conventional methods. In embodiments in which the entire volume of sample is not retracted past the sampling valve 62, gas is prevented from retracting past the sampling valve. Such gas interferes with accuracy and precision of dispensed sample volumes. Further, for given hardware of the system (e.g., given size tubing and sampling needle), the methods allow for sampling a relative small sample volume while controllably depressurizing the sample. Such sample volumes may range from about 25 to about 100 microliters or even as low as 5 microliters. By purging the antechamber with an inert gas during sampling, an inert gas, an inert gas atmosphere may be maintained in the reaction vessel 9 during and after sampling. Further, the parallel reactor system 10 described above may be used with reagents that are corrosive, and/or to produce reaction products that are corrosive. The sampling protocol may prevent uncontrolled release of corrosive material from the sampling needle (e.g., release on other reactor system components which may cause corrosion). The reactor system may be configured to reduce the amount of corrosive material that may escape from reagent storage or from the reaction vessel during or after injecting the corrosive material. For purposes of the present disclosure, the term "corrosive" includes materials that cause oxidation or other weakening of common reactor system components causing the components to need to be replaced prior to their expected useful life. Such corrosive materials include materials that themselves are corrosive and/or that may react with ambient materials such as water vapor or oxygen or may react with other reaction reagents to create a corrosive material.

When introducing elements of the present disclosure or the embodiment(s) thereof, the articles "a", "an", "the" and "said" are intended to mean that there are one or more of the elements. The terms "comprising," "including," "containing" and "having" are intended to be inclusive and mean that there may be additional elements other than the listed elements. The use of terms indicating a particular orientation (e.g., "top", "bottom", "side", etc.) is for convenience of description and does not require any particular orientation of the item described.

As various changes could be made in the above constructions and methods without departing from the scope of the disclosure, it is intended that all matter contained in the above description and shown in the accompanying drawing[s] shall be interpreted as illustrative and not in a limiting sense.

What is claimed is:

1. A method for sampling a non-atmospheric reaction vessel of a parallel reactor system, the reactor system including a reactor array and a sampling system, wherein the reactor array comprises a plurality of reaction vessels, a plurality of antechambers, wherein each antechamber is disposed above each reaction vessel, an antechamber sealing member associated with each reaction vessel, and a port valve disposed between each antechamber and an associated reaction vessel, and wherein the sampling system samples material from the plurality of reaction vessels and comprises a plurality of sampling pumps, a plurality of sampling needles, each sampling needle having a tip, and a plurality of sampling valves, wherein each sampling valve is disposed between each sampling pump and an associated needle tip, the method comprising:

lowering each sampling needle into an associated antechamber to form a substantially fluid-tight seal between an associated antechamber sealing member and each sampling needle;

lowering each sampling needle into an associated reaction vessel, each reaction vessel having a reactor material therein;

introducing the reactor material from each reaction vessel into an associated sampling needle to form a sampling slug in each sampling needle;

raising each sampling needle to position the tip of each sampling needle in an associated antechamber;

closing each port valve after each sampling needle tip is positioned in an associated antechamber;

retracting each sampling slug so that a first portion of each sampling slug is disposed between each sampling valve and an associated sampling pump and a second portion of each sampling slug is disposed between each sampling valve and the tip of an associated sampling needle; and discharging each sampling slug into a target substrate.

2. The method as set forth in claim 1, further comprising depressurizing each antechamber after retracting each sampling slug.

3. The method as set forth in claim 1, wherein the second portion of each sampling slug disposed between each sampling valve and an associated sampling needle tip upon retracting each sampling slug is suspended in the sampling system by surface tension.

4. The method as set forth in claim 1, further comprising equalizing the pressure between each antechamber and an associated reaction vessel after lowering each sampling needle into an associated antechamber and prior to lowering each sampling needle into an associated reaction vessel.

5. The method as set forth in claim 4, wherein each port valve is closed during equalizing such that each antechamber is isolated from an associated reaction vessel, the method further comprising opening each port valve prior to lowering each sampling needle into an associated reaction vessel.

6. The method as set forth in claim 4, wherein each antechamber is pressurized.

7. The method as set forth in claim 1, further comprising purging fluid from each antechamber after lowering each sampling needle into an associated antechamber and prior to lowering each sampling needle into an associated reaction vessel.

8. The method as set forth in claim 7, wherein fluid is purged from each antechamber after lowering each sampling needle into an associated antechamber by circulating inert gas through each antechamber.

9. The method as set forth in claim 1, wherein discharging each sampling slug into a target substrate comprises:
    opening each sampling valve; and
    operating each sampling pump to allow the reactor material to discharge into the target substrate.

10. The method as set forth in claim 9, wherein the target substrate is an analysis vessel or analytical device.

11. The method as set forth in claim 9, further comprising purging vapor or fluid from each antechamber after each port valve is closed.

12. The method as set forth in claim 11, wherein the vapor or fluid is purged from each antechamber after each port valve is closed by circulating inert gas through each antechamber.

13. The method as set forth in claim 12, wherein each reaction vessel includes an inert atmosphere prior to lowering each sampling needle into an associated antechamber and the inert atmosphere is maintained at least until each port valve is closed.

14. The method as set forth in claim 1, further comprising opening each port valve after lowering each sampling needle into an associated antechamber and prior to lowering each sampling needle into an associated reaction vessel.

15. The method as set forth in claim 14, wherein discharging each sampling slug into a target substrate comprises:
    raising each sampling needle such that each sampling needle tip disengages an associated antechamber sealing member; and
    positioning each sampling needle above the target substrate.

16. The method as set forth in claim 15, wherein the pressure in each reaction vessel is above atmospheric pressure.

17. The method as set forth in claim 1, wherein the reactor system comprises a housing in which the reactor array is mounted, the pressure of each reaction vessel exceeding the pressure in the housing.

18. The method as set forth in claim 1, wherein the pressure in each reaction vessel is below atmospheric pressure.

19. The method as set forth in claim 1, wherein the reactor system comprises a housing in which the reactor array is mounted, the pressure of each reaction vessel being less than the pressure in the housing.

20. The method as set forth in claim 1, wherein each sampling pump is a syringe pump.

\* \* \* \* \*